United States Patent [19]

Duke

[11] 4,358,437

[45] Nov. 9, 1982

[54] COMPOSITIONS

[75] Inventor: Susan A. Duke, Croydon, England

[73] Assignee: Beecham Group Limited, England

[21] Appl. No.: 253,360

[22] Filed: Apr. 13, 1981

Related U.S. Application Data

[63] Continuation of Ser. No. 98,051, Nov. 28, 1979, abandoned.

[30] Foreign Application Priority Data

Nov. 29, 1978 [GB] United Kingdom ............... 48530/78

[51] Int. Cl.$^3$ ................................................ A61K 7/18
[52] U.S. Cl. ......................................... 424/52; 424/49
[58] Field of Search .......................................... 424/52

[56] References Cited

U.S. PATENT DOCUMENTS

| | | | |
|---|---|---|---|
| 1,275,275 | 8/1918 | Levinson | 424/49 |
| 3,151,027 | 9/1964 | Cooley et al. | 424/52 |
| 3,955,942 | 5/1976 | Cordon et al. | 424/49 |
| 3,966,863 | 6/1976 | Forward et al. | 424/52 |
| 3,980,767 | 9/1976 | Chown et al. | 424/52 |
| 4,038,380 | 7/1977 | Cordon | 424/49 |
| 4,141,969 | 2/1979 | Mitchell | 424/52 |
| 4,181,633 | 1/1980 | Colodney et al. | 424/49 X |

*Primary Examiner*—Shep K. Rose
*Attorney, Agent, or Firm*—Jacobs & Jacobs

[57] ABSTRACT

A toothpaste contains 2% by weight of calcium metasilicate, 0.80% of sodium monofluorophosphate and 44.77% calcium carbonate. The presence of calcium metasilicate in combination with the monofluorophosphate and carbonate increases the fluoride uptake over and above that which is expected from the level of free fluoride present.

10 Claims, No Drawings

COMPOSITIONS

CROSS-REFERENCE

This is a continuation of Ser. No. 098,051, filed Nov. 28, 1979, now abandoned.

This invention relates to oral hygiene compositions having anti-cariogenic activity, and more particularly to toothpastes, and mouthwashes.

It has been recognised for some years that the incorporation of ionic fluoride compounds into oral hygiene compositions such as toothpastes and mouthwashes provides them with anti-cariogenic activity. This activity is believed to result from the ability of fluoride to reduce the solubility of tooth enamel in slightly acid media which frequently occur in the mouth as a result of the action of bacteria on food. This solubility-reducing effect is thought to result from the conversion of hydroxyapatite, a principal mineral component of tooth enamel, into a less soluble mineral, fluoroapatite.

It is generally recognised that ionic monofluorophosphates are the most effective anti-cariogenic fluoridating agents. It is thought in some quarters that monofluorophosphates exert their effect at least in part, by hydrolysing to phosphate and fluoride ion, which is subsequently incorporated into tooth enamel.

It has been found that the presence of certain quantities of carbonate ion and metasilicate ion in a solution containing dissolved monofluorophosphate ion increases the quantity of free fluoride ion concentration available in solution and that when teeth are treated by such solutions, not only is there an increase in fluoride uptake over and above that which would be expected for the level of free fluoride present, but also there is a significant decrease in the dissolution rate of tooth enamel mineral after such treatment as compared with that expected for the level of free fluoride ions.

These effects are principally dependent upon the amount of dissolved metasilicate ion which is formed in the mouth, usually by dilution of an oral hygiene composition with saliva.

The effects are not seen in the presence of alumina.

According to the present invention there is provided an oral hygiene composition, substantially free of alumina, comprising a source of metasilicate ions, a source of carbonate ions and a source of monofluorophosphate ions, the sources being present in amounts such that, in use, an aqueous solution containing from 3.5 to $7.0 \times 10^{-4}$ mol.l$^{-1}$ dissolved metasilicate ions, from 1.0 to $2 \times 10^{-2}$ mol.l$^{-1}$ dissolved monofluorophosphate ions and from $0.5 \times 10^{-4}$ to $1.0 \times 10^{-3}$ mol.l$^{-1}$ dissolved carbonate ions is produced in the mouth.

Preferably the concentration of metasilicate ions is about $5 \times 10^{-4}$ mol.l.

The source of metasilicate ions may be silicic acid or a physiologically acceptable salt thereof which is at least sparingly soluble in aqueous media. Examples of such salts include alkaline earth metal salts such as calcium and magnesium metasilicate. Calcium metasilicate is a particularly preferred source of ions.

The source of monofluorophosphate ions is suitably a physiologically acceptable salt which is soluble in aqueous media. Examples of such salts include alkali metal monofluorophosphates of which sodium monofluorophosphate Na$_2$PO$_3$F is especially preferred.

The source of carbonate ions is also a soluble or sparingly soluble physiologically acceptable carbonate salt. Examples include alkali metal salts such as sodium and potassium carbonate and alkaline earth metal salts such as magnesium and calcium carbonate.

The preferred form of oral hygiene composition according to the invention is a toothpaste, which becomes extensively diluted by saliva in normal use. The degree of dilution in the mouth of a fluoride-containing toothpaste can be determined by the following standard test. A standard amount, viz 1 gm, of toothpaste containing a known amount of fluoride is dispensed onto a toothbrush. A volunteer uses this to brush his teeth for 30 seconds, and spits the contents of his mouth into a pre-weighed receiver. The weight of spittings can be measured and the concentration of fluoride in the spittings can be determined by estimating the total fluoride present.

In practice it is found that a toothpaste becomes diluted about four fold by saliva when in use.

In general, when it is desired to apply a soluble active material in certain concentrations to teeth via a toothpaste, the paste is formulated four times more concentrated than the final concentration required in the mouth, to account for this dilution effect.

According to a further aspect of the invention, there is provided a toothpaste, substantially free of alumina, comprising from 1.5 to $3 \times 10^{-3}$ mol.l$^{-1}$ of dissolved metasilicate ions, from 4 to $8 \times 10^{-2}$ mol.l$^{-1}$ dissolved monofluorophosphate ions and from $2 \times 10^{-4}$ to $4 \times 10^{-3}$ mol.l$^{-1}$ dissolved carbonate ions in an aqueous toothpaste vehicle.

More suitably the composition contains not more than $6 \times 10^{-2}$ mol.l$^{-1}$ and preferably contains $5 \times 10^{-2}$ mol.l$^{-1}$ of dissolved monofluorophosphate ions.

The quantity of dissolved carbonate ions present in toothpastes according to this invention is generally not less than $2 \times 10^{-4}$ mol.l$^{-1}$ but is more suitably $5 \times 10^{-4}$ to $10 \times 10^{-4}$ mol.l$^{-1}$. Typically, a toothpaste formulation consists of an aqueous dispersion comprising an abrasive cleaning and/or polishing agent, a surfactant, a humectant, a thickener, and optionally flavouring and sweetening agents.

Typically, a toothpaste having the above concentrations of dissolved metasilicate, monofluorophosphate and carbonate ions comprises from 1.2 to 3.5% by weight of calcium metasilicate, from 0.6 to 1.2% by weight of an ionic monofluorophosphate, and from 10 to 60% by weight of calcium carbonate, in an aqueous toothpaste vehicle. The preferred weight range of calcium metasilicate is from 1.2 to 2.4%. Most preferably, the amount of calcium metasilicate in the toothpaste is 2% by weight.

With the exception of aluminas any conventional toothpaste abrasive may be used in accordance with this invention. Powdered forms of calcium carbonate in an abrasive form constitute one important class of such abrasives. Examples of these abrasives are milled limestone or marble, chalks such as aragonite, calcite or mixtures thereof, and synthetically precipitated chalks such as waterworks chalk. Generally, the calcium carbonate should have a weight median diameter of less than 40 microns, preferably less than 15 microns.

A second class of abrasives are powdered silicas, particularly, silica xerogels as defined in U.S. Pat. No. 3,538,230.

Abrasive agents of the above two classes may be used alone or in admixture with each other or in admixture with other abrasive agents such as water insoluble sodium or potassium metaphosphates, hydrated or anhydrous dicalcium phosphate, calcium pyrophosphate, zirconium silicate or mixtures thereof.

Typically toothpaste formulations comprise 20 to 75% by weight of abrasive.

When the abrasive is a carbonate such as a chalk, it may also act as the carbonate ion source. However it may be desired to supplement the quantity of carbonate ion by adding a soluble carbonate salt such as sodium carbonate to the formulation. Of course where the abrasive is other than a carbonate abrasive, addition of a non-abrasive sparingly soluble or soluble carbonate is essential. The necessary quantity of dissolved carbonate ion present where a sparingly soluble carbonate is employed may be calculated from a knowledge of its solubility constant. However, it is generally more practical in view of the number of constituents which a toothpaste contains to make a four fold dilution of the formulation with water and to measure the amount of dissolved carbonate in that solution.

The surfactant is normally a water-soluble non-soap or synthetic organic detergent. Suitable surfactants include the water-soluble salts of: higher fatty acid monoglyceride monosulphates (for example sodium hydrogenated coconut fatty acid monoglyceride monosulphate); higher alkyl sulphates (for example sodium lauryl sulphate); alkylarylsulphonates (for example sodium dodecylbenzenesulphonates); and higher alkyl sulphoacetates (for example sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amides of glycine, sarcosine, alanine, 3-aminopropanoic acid and valine, particularly the N-lauroyl, myristoyl and palmitoyl sarcosinate compounds. Conventional non-ionic surfactants may also be included if desired.

The surface-active materials are generally present in an amount of 0.05 to 10%, preferably 0.5 to 5% by weight of the composition.

Typical humectants which may be used in toothpastes in accordance with this invention include glycerine, sorbitol and propylene glycol, either alone or in admixture with each other. It is preferred to use mixtures of sorbitol and glycerine. Typically, the total liquid content of a toothpaste, that is to say, water and humectant is 20 to 75% by weight of the preparation.

Typical thickening agents which may be used in toothpastes in accordance with this invention include natural and synthetic gums, and gum-like materials such as Irish Moss, gum tragacanth, sodium carboxymethylcellulose, polyvinylpyrrolidone, or starch. Irish Moss and sodium carboxymethylcellulose are preferred. Generally the gum content is less than 10% by weight of the formulation and is preferably 0.5 to 5% by weight.

Materials which toothpaste formulations according to the invention may optionally contain are sweeteners such as saccharin; flavouring agents such as oils of spearmint, wintergreen or peppermint, chloroform, colouring or whitening agents such as titanium dioxide; preservatives such as sodium benzoate; emulsifying agents; acidifying agents such as citric acid; silicones; alcohol; menthol; chlorophyll compounds such as sodium copper chlorophyllin, and anti-bacterial agents such as chlorhexidine.

If desired, the toothpaste may be formulated as cored or striped toothpaste compositions, particularly with an opaque core or stripes (containing the calcium carbonate abrasive and the metasilicate ingredient) within or on a transparent gel. The gel can contain the monofluorophosphate ingredient and in such cases the composition is taken as a whole in determining proportions of ingredients as aforesaid.

The pH of toothpastes according to this invention is mildly alkaline, that is to say, the pH is between 8.5 and 10.5.

Toothpastes in accordance with this invention are prepared in the usual way.

The invention is now described in more detail with reference to the following examples showing the effect of increasing calcium metasilicate concentration in a toothpaste composition on the fluorohydroxyapatite formation in tooth enamel.

EXAMPLE 1

A toothpaste having the following formulation was made up:

|  | % W/W |
| --- | --- |
| Glycerin | 15.63 |
| Sorbitol (70% solution) | 10.40 |
| Carboxymethyl cellulose gum | 0.75 |
| Hydroxyethyl cellulose gum | 0.07 |
| Sodium saccharin (15% solution) | 1.00 |
| Sodium monofluorophosphate | 0.80 |
| Chalk abrasive | 44.77 |
| Sodium lauryl sulphate | 1.77 |
| Flavour ingredients | 1.00 |
| Calcium metasilicate | 2.00 |
| Water | to 100.00 |

A mucilage was first prepared by blending the carboxymethyl cellulose, hydroxyethyl cellulose and calcium metasilicate. The mixture, together with the saccharin, glycerin and sorbitol, was placed in a suitable mixing vessel fitted with a high shear mixer, and mixing was carried out until a homogeneous distribution was obtained. Water, pre-heated to 55° C., was then added followed by sodium monofluorophosphate, and mixing was continued. The mixture was allowed to stand to permit the gums to hydrate. The flavour was then added and mixed in. The chalk abrasive was then added whilst under partial vacuum conditioning followed by the lauryl sulphate, and mixing was carried out until a homogeneous paste was obtained. Similar formulations having 0.2%, 0.5%, 1.0% and 5% calcium metasilicate were prepared, and the fluorohydroxyapatite formation (FHA) for each formulation was measured following a minute treatment of the enamel mineral, according to the method described in Caries Research Vol. 12, pages 12 to 20 (1978). The FHA values were plotted against the percentages by weight of calcium metasilicate in the toothpastes. The results demonstrate that the most effective percentage range of calcium metasilicate in the toothpaste was from about 1.2 to 3.5% by weight, and the preferred amount was 2%.

Further examples are as follows:

EXAMPLE 2

A striped toothpaste having the following formulation was made up:

| Clear Gel Phase | % W/W |
| --- | --- |
| Synthetic magnesium lithium silicate clay | 4.17 |
| Sorbitol (70% solution) | 60.00 |

| Clear Gel Phase | % W/W |
| --- | --- |
| Polyethylene glycol 300 | 4.00 |
| Sodium carboxymethyl cellulose gum | 1.30 |
| Silica (colloidal) | 2.00 |
| Sodium monofluorophosphate | 0.80 |
| Saccharin | 0.15–0.25 |
| Flavour | 0.5–1.5 |
| Sodium lauryl sulphate | 1.5–2.5 |
| Water soluble dye | q.s. |
| Water to | 100.00 |

| Opaque Paste Phase | % W/W |
| --- | --- |
| Sorbitol (70% solution) | 34.00 |
| Synthetic magnesium lithium silicate clay | 2.00 |
| Sodium carboxymethyl cellulose | 0.70 |
| Polyethylene glycol 300 | 2.00 |
| Titanium dioxide | 0.50 |
| Flavour | 0.5–1.5 |
| Chalk abrasive | 38.84 |
| Sodium monofluorophosphate | 0.80 |
| Saccharin | 0.15–0.25 |
| Silica (colloidal) | 1.0 |
| Sodium lauryl sulphate | 1.5–2.5 |
| Calcium metasilicate | 3.16 |
| Water to | 100.00 |

Preparation of the Clear Gel Phase

Carboxymethyl cellulose was slurried with part of the polyethylene glycol 300 and this, together with the flavour and the silica, was slurried in part of the sorbitol in a vacuum mixing vessel. After mixing, the saccharin and sodium monofluorophosphate, each separately predissolved in water, were added and the mixing was continued.

A dispersion of magnesium lithium silicate with part of the water, sorbitol and polyethylene glycol 300 was prepared and added to the vacuum mixing vessel. Mixing was carried out until a homogeneous clear gel was obtained.

Preparation of the Opaque Paste Phase

A mucilage was prepared by blending the magnesium lithium silicate clay with the water, part of the sorbitol and the titanium dioxide. The mucilage was transferred, with the flavour, to a suitable vacuum mixing vessel. After mixing under vacuum, the chalk abrasive and calcium metasilicate were added followed by the sodium monofluorophosphate and saccharin (each separately predissolved in water), the silica slurried in part of the sorbitol and finally the sodium lauryl sulphate dissolved in water. Mixing was continued until a uniform paste was obtained. A striped product was obtained by combining the gel and paste phases using a tube filling machine.

EXAMPLE 3

A striped toothpaste having the following formulation was made up:

| Clear Gel Phase | % W/W |
| --- | --- |
| Polyethylene glycol 400 | 3.00 |
| Sodium carboxymethyl cellulose | 1.20 |
| Calcium carrageenan gum | 0.30 |
| Sorbitol (70% solution) | 59.64 |
| Saccharin | 0.05–0.10 |
| Calcium glycerophosphate | 0.21 |
| Sodium monofluorophosphate | 0.76 |
| Sodium benzoate | 0.20 |
| Sodium silicate solution | 0.20 |
| Water soluble dye(s) | q.s. |
| Precipitated silica | 15.00 |
| Flavour | 0.5–1.0 |
| Sodium lauryl sulphate | 1.0–1.5 |
| Water to | 100.00 |

| Opaque Paste Phase | % W/W |
| --- | --- |
| Polyethylene glycol 400 | 2.94 |
| Sodium carboxymethyl cellulose | 0.65 |
| Sodium monofluorophosphate | 0.76 |
| Sorbitol (70% solution) | 35.82 |
| Saccharin | 0.05–0.10 |
| Sodium benzoate | 0.20 |
| Calcium metasilicate | 3.16 |
| Calcium carbonate abrasive | 38.8 |
| Titanium dioxide | 0.50 |
| Precipitated silica | 5.00 |
| Flavour | 0.5–1.0 |
| Sodium lauryl sulphate | 1.0–1.5 |
| Water to | 100.00 |

Preparation of the Clear Gel Phase

The saccharin, sodium benzoate, sodium monofluorophosphate and the dye(s) were dissolved in a mixture of the water and part of the sorbitol. This solution was combined under vacuum with a dispersion of sodium carboxymethyl cellulose and calcium carrageenan in polyethylene glycol in a suitable vacuum mixing vessel. The precipitated silica, calcium glycerophosphate, flavour, and sodium lauryl sulphate were then added with separate mixing after each addition.

Preparation of the Opaque Paste Phase

The sodium monofluorophosphate, saccharin and sodium benzoate in the water and sorbitol were mixed in a suitable vacuum mixing vessel.

The sodium carboxymethyl cellulose, dispersed in polyethylene glycol was added and mixed under vacuum. The calcium carbonate, titanium dioxide, calcium metasilicate and precipitated silica were blended and added to the main mix and mixed under vacuum. The flavour and sodium lauryl sulphate were then added with mixing between each addition.

A striped product was obtained by combining the gel and paste phases using a tube filling machine.

I claim:

1. An anticariogenic oral hygiene composition substantially free of alumina and having improved fluoride release from monofluorophosphate, comprising a source of monofluorophosphate ions, a source of carbonate ions and a source of metasilicate ions, each source being present in an amount such that, in use, an aqueous solution containing from 3.5 to $7.0 \times 10^{-4}$ mol.l$^{-1}$ dissolved metasilicate ions, from 1 to $2 \times 10^{-2}$ mol.l$^{-1}$ dissolved monofluorophosphate ions and from $0.5 \times 10^{-4}$ to $1 \times 10^{-3}$ mol.l$^{-1}$ dissolved carbonate ions is produced in the mouth.

2. An anticariogenic oral hygiene composition according to claim 1, in which the concentration of metasilicate ions is about $5 \times 10^{-4}$ mol.l$^{-1}$.

3. An anticariogenic oral hygiene composition according to claim 1 in which the metasilicate source is calcium metasilicate.

4. An anticariogenic toothpaste, substantially free of alumina, comprising a source of monofluorophosphate ions, a source of carbonate ions and a source of metasilicate ions in an aqueous toothpaste vehicle, in which the ionic concentrations of dissolved monofluorophosphate, carbonate and metasilicate ions are from 4 to $8 \times 10^{-2}$ mol.l$^{-1}$, from $2 \times 10^{-4}$ to $4 \times 10^{-3}$ mol.l$^{-1}$ and from 1.5 to $3 \times 10^{-3}$ mol.l$^{-1}$ respectively.

5. An anticariogenic toothpaste according to claim 4, in which not more than $6 \times 10^{-2}$ mol.l$^{-1}$ of dissolved monofluorophosphate ions are present.

6. An anticariogenic toothpaste according to claim 4, in which from $5 \times 10^{-4}$ to $10 \times 10^{-4}$ mol.l$^{-1}$ of dissolved carbonate ions are present.

7. An anticariogenic toothpaste according to claim 4, comprising from 1.2 to 3.5% by weight of calcium metasilicate, from 10 to 60% by weight of calcium carbonate, and from 0.6 to 1.2% by weight of an ionic monofluorophosphate, in an aqueous toothpaste vehicle.

8. An anticariogenic toothpaste according to claim 7 which contains about 2% by weight of calcium metasilicate.

9. A method of increasing the fluoride uptake by tooth enamel, which method comprises treating teeth with an anticariogenic, oral-hygiene composition according to claim 1, in about a fourfold amount prior to dilution by saliva in the mouth.

10. An anticariogenic toothpaste according to claim 4, in which the ionic sources are present in about a fourfold amount before dilution by the saliva of the mouth.

* * * * *